(12) United States Patent
Scaia et al.

(10) Patent No.: US 7,687,663 B2
(45) Date of Patent: Mar. 30, 2010

(54) RECOVERY OF NOBLE METALS FROM AQUEOUS PROCESS STREAMS

(75) Inventors: Mark D. Scaia, St. Louis, MO (US); David R. Eaton, Kirkwood, MO (US); Roger J. Hoekstra, St. Louis, MO (US); Eric A. Haupfear, St. Charles, MO (US)

(73) Assignee: Monsanto Technology LLC, St. Louis, MO (US)

( * ) Notice: Subject to any disclaimer, the term of this patent is extended or adjusted under 35 U.S.C. 154(b) by 720 days.

(21) Appl. No.: 11/273,410

(22) Filed: Nov. 14, 2005

(65) Prior Publication Data

US 2006/0106248 A1    May 18, 2006

Related U.S. Application Data

(60) Provisional application No. 60/627,668, filed on Nov. 12, 2004.

(51) Int. Cl.
    *C07F 9/22*    (2006.01)
(52) U.S. Cl. .......................... 562/17; 502/10
(58) Field of Classification Search ............. 562/17; 502/10
    See application file for complete search history.

(56) References Cited

U.S. PATENT DOCUMENTS

| | | | |
|---|---|---|---|
| 3,799,758 A | 3/1974 | Franz | |
| 3,950,402 A | 4/1976 | Franz | |
| 3,969,398 A | 7/1976 | Hershman | |
| 3,975,189 A | 8/1976 | Haugen | |
| 3,975,247 A | 8/1976 | Stralser | |
| 3,985,552 A | 10/1976 | Edwards | |
| 3,985,854 A | 10/1976 | Bradford et al. | |
| 3,999,983 A | 12/1976 | Grosbois et al. | |
| 4,039,327 A | 8/1977 | Dietz, Jr. et al. | |
| 4,041,126 A | 8/1977 | Baltz et al. | |
| 4,042,665 A | 8/1977 | Hatch | |

(Continued)

FOREIGN PATENT DOCUMENTS

EP    0472693 B1    11/1995

(Continued)

OTHER PUBLICATIONS

Sheals, J; Granström, M; Sjöberg, S; Persson, P; "Coadsorption of Cu(II) and Glyphosate at the Water-Goethite (α-FeOOH) Interface: Molecular Structures from FTIR and EXAFS Measurements," Journal of Colloid and Interface Science, 2003, pp. 38-47, vol. 262.

(Continued)

*Primary Examiner*—Sikarl A Witherspoon
*Assistant Examiner*—Chukwuma O Nwaonicha
(74) *Attorney, Agent, or Firm*—Senniger Powers LLP; Joseph A. Schaper

(57) ABSTRACT

This invention generally relates to processes for recovering solubilized noble metals from aqueous process streams, in particular, aqueous process streams generated in the preparation of an N-(phosphonomethyl)glycine product, for example, by noble metal-catalyzed oxidation of an N-(phosphonomethyl)iminodiacetic acid substrate. The process includes contacting the aqueous process stream with a noble metal adsorption media such as an ion exchange resin to remove solubilized noble metal from the process stream.

29 Claims, 2 Drawing Sheets

U.S. PATENT DOCUMENTS

| | | | |
|---|---|---|---|
| 4,069,040 A | 1/1978 | Thomas et al. |
| 4,077,800 A | 3/1978 | Peka et al. |
| 4,082,546 A | 4/1978 | Wallace |
| 4,092,154 A | 5/1978 | Dietz, Jr. et al. |
| 4,097,271 A | 6/1978 | Swinkels et al. |
| 4,105,742 A | 8/1978 | Edwards et al. |
| 4,108,639 A | 8/1978 | Lake et al. |
| 4,127,458 A | 11/1978 | MacGregor |
| 4,128,462 A | 12/1978 | Ghiringhelli et al. |
| 4,162,950 A | 7/1979 | MacGregor |
| 4,216,012 A | 8/1980 | Krofchak |
| 4,239,833 A | 12/1980 | Retmaniak et al. |
| 4,257,807 A | 3/1981 | Drobot |
| 4,261,738 A | 4/1981 | Valentine et al. |
| 4,289,531 A | 9/1981 | Lechavelier et al. |
| 4,302,317 A | 11/1981 | Mock |
| 4,337,226 A | 6/1982 | Peasley et al. |
| 4,384,889 A | 5/1983 | Wiewiorowski et al. |
| 4,388,279 A | 6/1983 | Quick |
| 4,397,686 A | 8/1983 | Winkler et al. |
| 4,400,250 A | 8/1983 | Fairhurst |
| 4,412,859 A | 11/1983 | Hatfield et al. |
| 4,426,251 A | 1/1984 | Ida et al. |
| 4,450,188 A | 5/1984 | Kawasumi |
| 4,497,657 A | 2/1985 | Hatfield et al. |
| 4,510,027 A | 4/1985 | Wiewiorowski et al. |
| 4,511,539 A | 4/1985 | Stephenson |
| 4,526,614 A | 7/1985 | Beshty et al. |
| 4,548,791 A | 10/1985 | Fletcher et al. |
| 4,571,262 A | 2/1986 | Kerfoot et al. |
| 4,582,650 A | 4/1986 | Felthouse |
| 4,592,779 A | 6/1986 | Russ et al. |
| 4,612,388 A | 9/1986 | Mita et al. |
| 4,624,937 A | 11/1986 | Chou |
| 4,662,613 A | 5/1987 | Woog |
| 4,666,212 A | 5/1987 | Loveday et al. |
| 4,670,052 A | 6/1987 | Stanley et al. |
| 4,696,772 A | 9/1987 | Chou |
| 4,725,313 A | 2/1988 | Adamson |
| 4,726,841 A | 2/1988 | Grant et al. |
| 4,726,939 A | 2/1988 | Touro |
| 4,778,519 A | 10/1988 | Pesic |
| 4,814,007 A | 3/1989 | Lin et al. |
| 4,880,511 A | 11/1989 | Sugita |
| 4,892,631 A | 1/1990 | White |
| 4,895,597 A | 1/1990 | Lin et al. |
| 4,900,520 A | 2/1990 | Behnam et al. |
| 4,911,804 A | 3/1990 | Dickson |
| 4,941,917 A | 7/1990 | Cenegy et al. |
| 4,992,200 A | 2/1991 | Lin et al. |
| 4,992,207 A | 2/1991 | Darnall et al. |
| 5,045,290 A | 9/1991 | Harris et al. |
| 5,082,492 A | 1/1992 | Gallup et al. |
| 5,087,740 A | 2/1992 | Smith |
| 5,102,632 A | 4/1992 | Allen et al. |
| 5,116,415 A | 5/1992 | Rinehart |
| 5,122,185 A | 6/1992 | Hochella et al. |
| 5,147,841 A | 9/1992 | Wilcoxon |
| 5,151,224 A | 9/1992 | Madou et al. |
| 5,160,711 A | 11/1992 | Atkinson et al. |
| 5,179,228 A | 1/1993 | Martin Ramon et al. |
| 5,201,942 A | 4/1993 | Demopoulos et al. |
| 5,208,194 A | 5/1993 | Pitchai et al. |
| 5,213,609 A | 5/1993 | Hyde et al. |
| 5,215,575 A | 6/1993 | Butler |
| 5,246,486 A | 9/1993 | Brierley et al. |
| 5,250,166 A | 10/1993 | Motojima et al. |
| 5,252,305 A | 10/1993 | Ezawa et al. |
| 5,256,187 A * | 10/1993 | Gefvert ................. 75/717 |
| 5,284,633 A | 2/1994 | Gefvert |
| 5,292,490 A | 3/1994 | Duyvesteyn et al. |
| 5,302,183 A | 4/1994 | De Boer et al. |
| 5,304,233 A | 4/1994 | Awadalla et al. |
| 5,328,669 A | 7/1994 | Han et al. |
| 5,338,338 A | 8/1994 | Kohr |
| 5,354,359 A | 10/1994 | Wan et al. |
| 5,354,458 A | 10/1994 | Wang et al. |
| 5,364,444 A | 11/1994 | McDoulett, Jr. et al. |
| 5,364,453 A | 11/1994 | Kohr |
| 5,405,430 A | 4/1995 | Groves et al. |
| 5,411,573 A | 5/1995 | Kang et al. |
| 5,439,503 A | 8/1995 | Burr |
| 5,443,621 A | 8/1995 | Kohr |
| 5,449,397 A | 9/1995 | Hunter et al. |
| 5,605,563 A | 2/1997 | Kidby et al. |
| 5,606,107 A | 2/1997 | Smith |
| 5,612,431 A | 3/1997 | Waddell et al. |
| 5,626,647 A | 5/1997 | Kohr |
| 5,672,194 A | 9/1997 | Hunter et al. |
| 5,690,806 A | 11/1997 | Sunderland et al. |
| 5,785,736 A | 7/1998 | Thomas et al. |
| 5,792,235 A | 8/1998 | Kohr |
| 5,827,348 A | 10/1998 | Waddell et al. |
| 5,939,034 A | 8/1999 | Virnig et al. |
| 5,942,098 A | 8/1999 | Sekissov et al. |
| 6,005,140 A * | 12/1999 | Morgenstern et al. ......... 562/17 |
| 6,197,214 B1 | 3/2001 | Virnig et al. |
| 6,232,494 B1 | 5/2001 | Morgenstern et al. |
| 6,274,045 B1 | 8/2001 | Kreisler |
| 6,315,812 B1 | 11/2001 | Fleming et al. |
| 6,364,931 B1 | 4/2002 | Robinson et al. |
| 6,413,389 B1 | 7/2002 | Shih et al. |
| 6,417,133 B1 | 7/2002 | Ebner et al. |
| 6,440,194 B1 | 8/2002 | Krofchak et al. |
| 6,444,010 B1 | 9/2002 | Watanabe |
| 6,455,018 B1 | 9/2002 | Cuif |
| 6,500,231 B1 | 12/2002 | Wan |
| 6,551,378 B2 | 4/2003 | Farone et al. |
| 6,579,504 B1 | 6/2003 | Liddell |
| 6,586,621 B2 | 7/2003 | Leiber et al. |
| 6,603,039 B1 | 8/2003 | Ebner et al. |
| 6,730,813 B2 * | 5/2004 | Hitzler et al. ................. 568/17 |
| 6,927,304 B2 | 8/2005 | Leiber |
| 6,956,005 B2 | 10/2005 | Leiber |
| 7,179,936 B2 * | 2/2007 | Haupfear et al. ............... 562/17 |
| 2002/0068836 A1 | 6/2002 | Haupfear et al. |
| 2004/0026329 A1 | 2/2004 | Ekman et al. |
| 2004/0102658 A1* | 5/2004 | Brown et al. ................. 568/913 |

FOREIGN PATENT DOCUMENTS

| | | |
|---|---|---|
| JP | 2001279343 | 10/2001 |
| JP | 2002097193 A | 4/2002 |
| JP | 2005002414 A | 1/2005 |
| WO | WO 00/09520 A1 | 2/2000 |

OTHER PUBLICATIONS

Appleton, et al., "Amino Acid Complexes of Platinum(IV). I. Trimethylplatinum(IV) Complexes with Glycinate, Iminodiacetate, N-Methyliminodiacetate, Nitrilotriacetate, and Ethylenediamine-Tetraacetate," Inorganica Chimica Acta, 1978, pp. 89-99, vol. 29, Switzerland.

Appleton, "Donor Atom Preferences in Complexes of Platinum and Palladium with Amino Acids and Related Molecules," Coordination Chemistry Reviews 166, 1997, pp. 313-359.

Appleton, et al., "Multinuclear NMR Study of Reactions of Methylphosphonic Acid, $CH_3PO_3H_2$, and (Aminoalkyl) Phosphonic Acids, $NH_2(CH_2)nPO_3H_2$ (n=1-3), with the cis-Diamminediaquaplatinum(II) Cation and cis-Diamminedihydroxoplatinum(II)," Inorganic Chemistry, 1986, pp. 720-725, vol. 25, No. 6, Brisbane, Australia.

Appleton, et al. "NMR Spectra of Iminobis (methylenephosphonic acid), $HN(CH_2PO_3H_2)_2$, and Related Ligands and of Their Complexes with Platinum(II)," Inorganic Chemistry, 1986, pp. 726-734, vol. 25, No. 6, Brisbane, Australia.

Appleton, et al., "Platinum Complexes with Iminodiacetate and (Methylimino) Diacetate, Including Genuine Meridional Complexes," Inorganic Chemistry, 1985, pp. 666-672, vol. 24, No. 5, Brisbane, Australia.

Appleton, et al., "Platinum (II) Complexes with Glycine as an Oxygen-Bound Unidentate Ligand," J. Chem. Soc., Chem. Commun., 1983, pp. 911-913, Brisbane, Australia.

Crystal Structures of Three Dimethylplatinum(IV) Complexes with N-(Phosphonomethyl) Glycine Coordinated Facially, Inorganic Chemistry, 1994, pp. 444-455, vol. 33, No. 3, Brisbane, Australia.

Appleton, et al., "Reactions of Platinum(II) Aqua Complexes. 3. Multinuclear ($^{15}$N, $^{195}$Pt, $^{13}$C, and $^{1}$H) NMR Study of Reactions of Aqua and Hydroxo Complexes with Glycine and (Methylimino) Diacetic Acid[1]," Inorganic Chemistry, 1985, pp. 673-677, vol. 24, No. 5, Brisbane, Australia.

Battle, et al., "Synthesis, Spectroscopy, and Theoretical Studies of Platinum(II) Phosphate Complexes," J Chem Soc., Dalton, 2002, pp. 1898-1902, vol. 9.

Blaha, et al., "Complexes of Platinum(II) and Palladium(II) with Aminomethylphosphonic Acid and Glycylaminomethylphosphonic Acid," J Chem Soc Dalton, 1997, pp. 2621-2628, vol. 15.

Dow Chemical Company, "Column Separations Using Resins and Adsorbents," Tech Facts Lab Guide, Feb. 2001, pp. 1-9.

Dow Chemical Company, "Dowex Ion Exchange Resins Equilibrium Isotherm Testing for Liquid Phase Applications," Application Information Leaflet, May 1997.

Dow Chemical Company, "Dowex M-43 Ion Exchange Resin Corrosion Control with Dowex M-43 Ion Exchange Resin," Application Information Leaflet, Feb. 1999.

Erickson, et al., "Equilibrium and Kinetic Studies of Monoaquo Complexes of Platinum(II). 1. Formation from Corresponding *Chloro* Species by Hydrolysis," Inorganic Chemistry, 1987, pp. 992-997, vol. 26, No. 7.

Franz, et al., "Glyphosate: A Unique Global Herbicide," American Chemical Society Monograph 189, 1997, pp. 233-262.

Grumett, "Precious Metal Recovery from Spent Catalysts," Platinum Metals Rev., 2003, pp. 163-165, vol. 47, No. 4.

Hord, et al., "Improved Profitability Through Re$ource Recovery," Hydrocarbon Engineering, Dec. 2003.

McGarvey, et al., "Removal and Recovery of Metals by Ion Exchange," Catalog, 1985, pp. 1-10.

Nagao, et al., "Platinum(II) Complexes with Diglycine: X-ray Crystal Structure, $^{15}$N NMR Spectra, and Growth-Inhibitory Activity Against Mouse Meth A Solid Tumor in Vivo," Inorg Chem 36, 1997, pp. 4195-4201, vol. 19.

Purolite, "A-501P Macroporous Strong Base Anion Exchange Resin (for the removal of colloidal silica)," Technical Data Product Description, Apr. 1998.

Sagatys, et al., "Metal Complexes with N-(Phosphonomethyl) Glycine (Glyphosate): The Preparation and Characterization of the Group 2 Metal Complexes with Glyphosate and the Crystal Structure of Barium Glyphosate Dihydrate," Australian Journal of Chemistry, 2000, pp. 77-81, vol. 53, No. 2.

Schull, et al., "Synthesis and Characterization of Palladium(II) and Platinum(II) Complexes Containing Water-Soluble Hybrid Phosphine-Phosphonate Ligands," Inorganic Chemistry, 1996, pp. 6717-6723, vol. 35, No. 23.

* cited by examiner

RECOVERY OF NOBLE METALS FROM AQUEOUS PROCESS STREAMS

REFERENCE TO RELATED APPLICATION

This application claims benefit of U.S. provisional application Ser. No. 60/627,668 filed Nov. 12, 2004, the entire disclosure of which is incorporated herein by reference.

FIELD OF THE INVENTION

The present invention relates generally to techniques for recovering solubilized noble metals from aqueous process streams, in particular aqueous process streams generated in the preparation of an N-(phosphonomethyl)glycine product, for example, by the noble metal-catalyzed oxidation of an N-(phosphonomethyl)iminodiacetic acid substrate.

BACKGROUND OF THE INVENTION

N-(phosphonomethyl)glycine (known in the agricultural chemical industry as glyphosate) is described in Franz, U.S. Pat. No. 3,799,758. N-(phosphonomethyl)glycine and its salts are conveniently applied as a post-emergent herbicide in aqueous formulations. It is a highly effective and commercially important broad-spectrum herbicide useful in killing or controlling the growth of a wide variety of plants, including germinating seeds, emerging seedlings, maturing and established woody and herbaceous vegetation, and aquatic plants.

Various methods for making N-(phosphonomethyl)glycine products are known in the art. One of the more widely accepted methods of making N-(phosphonomethyl)glycine compounds includes the liquid phase oxidative cleavage of a carboxymethyl substituent from an N-(phosphonomethyl)iminodiacetic acid substrate using an oxygen-containing gas in the presence of a heterogeneous oxidation catalyst. As used herein, "N-(phosphonomethyl)iminodiacetic acid substrates" include N-(phosphonomethyl)iminodiacetic acid (sometimes referred to as PMIDA) and salts thereof, wherein the salt-forming cation is, for example, ammonium, alkylammonium, an alkali metal or an alkaline earth metal. For example, N-(phosphonomethyl)glycine may be prepared by the liquid phase oxidative cleavage of N-(phosphonomethyl)iminodiacetic acid with oxygen in accordance with the following reaction:

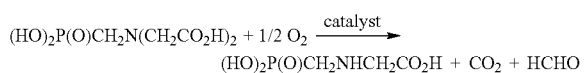

Other by-products also may form, such as formic acid, which is formed by the oxidation of the formaldehyde by-product, and aminomethylphosphonic acid (AMPA), which is formed by the oxidation of N-(phosphonomethyl)glycine. The preference for heterogeneous catalysis stems, at least in part, from the ease with which a particulate heterogeneous catalyst can normally be separated from the reaction product mixture for reuse following the oxidation. The literature is replete with examples of heterogeneous catalysis of N-(phosphonomethyl)iminodiacetic acid substrates in the production of N-(phosphonomethyl)glycine compounds. See generally, Franz, et al., *Glyphosate: A Unique Global Herbicide* (ACS Monograph 189, 1997) at pp. 233-62 (and references cited therein); Franz, U.S. Pat. No. 3,950,402; Hershman, U.S. Pat. No. 3,969,398; Felthouse, U.S. Pat. No. 4,582,650; Chou, U.S. Pat. Nos. 4,624,937 and 4,696,772; Ramon et al., U.S. Pat. No. 5,179,228; Ebner et al., U.S. Pat. No. 6,417,133 Leiber et al., U.S. Pat. No. 6,586,621 and Leiber, U.S. Pat. Nos. 6,927,304 and 6,956,005. The entire disclosure of the patents referred to in this paragraph and all other patents and publications referred to throughout this application are incorporated herein by reference.

High concentrations of formaldehyde in the reaction product solution resulting from oxidative cleavage of an N-(phosphonomethyl)iminodiacetic acid substrate are undesirable. The formaldehyde by-product is undesirable because it reacts with N-(phosphonomethyl)glycine to produce unwanted by-products, mainly N-methyl-N-(phosphonomethyl)glycine (NMG), which reduces the N-(phosphonomethyl)glycine yield. In addition, the formaldehyde by-product itself is undesirable because of its potential toxicity. See Smith, U.S. Pat. No. 5,606,107.

Franz, U.S. Pat. No. 3,950,402, discloses oxidizing the formaldehyde by-product to carbon dioxide and water simultaneously with the oxidative cleavage of the N-(phosphonomethyl)iminodiacetic acid substrate by using a heterogeneous oxidation catalyst comprising a noble metal deposited on a carbon support. The noble metal on carbon oxidation catalyst may be referred to as "bifunctional" in that the carbon component provides the primary adsorption site for the oxidation of the N-(phosphonomethyl)iminodiacetic acid substrate to form the N-(phosphonomethyl)glycine product and formaldehyde, while the noble metal component provides the primary adsorption site for the oxidation of formaldehyde and formic acid to form carbon dioxide and water, thus giving the following overall reaction:

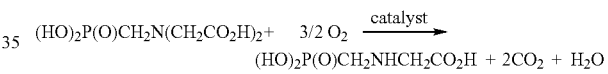

The noble metal component may also tend to reduce the rate of deactivation of the catalyst (i.e., prolong the useful life of the catalyst). In addition to the N-(phosphonomethyl)glycine product, formaldehyde, formic acid and unreacted N-(phosphonomethyl)iminodiacetic acid substrate, the oxidation product solution may also contain other by-products, such as N-methyl-N-(phosphonomethyl)glycine (NMG), N-formyl-N-(phosphonomethyl)glycine (NFG), aminomethylphosphonic acid (AMPA), methyl aminomethylphosphonic acid (MAMPA), iminodiacetic acid (IDA), glycine, glyoxylic acid, phosphoric acid, phosphorous acid and iminobis-(methylene)-bis-phosphonic acid (iminobis) and mixtures thereof.

Even though the Franz method produces an acceptable yield and purity of N-(phosphonomethyl)glycine, high losses of the costly noble metal by dissolution into the reaction mixture (i.e., leaching) typically result. Under the oxidation conditions of the reaction, some of the noble metal is oxidized into a more soluble form and organic components of the reaction solution, such as the N-(phosphonomethyl)iminodiacetic acid substrate and the N-(phosphonomethyl)glycine product, may act as ligands that solubilize the noble metal and/or sequester the solubilized noble metal in organic chelate complexes. After the N-(phosphonomethyl)glycine product has been formed and the noble metal catalyst has been separated from the reaction mixture, the oxidation product solution may be concentrated (e.g., by evaporation) to precipitate N-(phosphonomethyl)glycine product crystals and then separate the solid product from the various by-products and impurities retained in the resulting depleted reaction solution or mother liquor. Although a substantial quantity of the mother liquor may be recycled within the process, commercial considerations typically dictate that at least a portion of this residual reaction solution be purged from the system to avoid the build up of undesirable impurities and by-products that may compromise product purity. This purging unavoidably results in the loss of at least some of the solubilized noble metal and thereby undermines the economic feasibility of the process. Furthermore, the presence of solubilized noble metal within the reaction mixture typically results in incorporation of some noble metal into the N-(phosphonomethyl)glycine product resulting in additional loss of the noble metal.

Like Franz, Ramon et al., U.S. Pat. No. 5,179,228, teach using a noble metal deposited on the surface of a carbon support to catalyze the oxidative cleavage of an N-(phosphonomethyl)iminodiacetic acid substrate. To reduce the problem of noble metal leaching (reported to be as great as 30% noble metal loss per cycle) Ramon et al. teach flushing the reaction mixture with nitrogen under pressure after the oxidation reaction is completed to cause re-deposition of the noble metal onto the surface of the carbon support. According to Ramon et al., nitrogen flushing reduces the noble metal loss to less than 1%.

More recently, attention has focused on developing bifunctional noble metal on carbon oxidation catalysts that resist noble metal leaching (i.e., exhibit improved compositional stability) and provide increased activity and/or selectivity, particularly with respect to oxidation of formaldehyde into carbon dioxide and water (i.e., increased formaldehyde activity). Ebner et al., U.S. Pat. No. 6,417,133, disclose so-called "deeply reduced" noble metal on carbon catalysts for use in the oxidative cleavage of an N-(phosphonomethyl)iminodiacetic acid substrate and oxidation of other oxidizable reagents and methods for their preparation. Such deeply reduced catalysts exhibit remarkable resistance to noble metal leaching in aqueous, acidic oxidation reaction media. As a result, the catalyst disclosed by Ebner at al. provides for substantially quantitative oxidation of N-(phosphonomethyl)iminodiacetic acid substrates to N-(phosphonomethyl)glycine products, while minimizing noble metal losses and maintaining effective oxidation of the formaldehyde and formic acid by-products of the reaction for a prolonged period and/or over numerous oxidation cycles.

Although the teachings of Ebner et al. are significant and make economically practical the otherwise unavailable advantages provided by noble metal on carbon catalysts in the preparation of N-(phosphonomethyl)glycine products by oxidative cleavage of N-(phosphonomethyl)iminodiacetic acid substrates, noble metal losses in aqueous waste streams purged from the process and noble metal losses in N-(phosphonomethyl)glycine product streams cannot be completely avoided and represent a significant operational cost. That is, despite the improvement in catalyst stability and general resistance to noble metal leaching provided by the deeply reduced catalyst of Ebner et al., overall process economics are still diminished to some extent by the leaching of noble metal under the severe acidic oxidation reaction conditions which include the presence of the N-(phosphonomethyl)glycine product and other organic components that may act as ligands and exacerbate noble metal leaching even from stabilized bifunctional catalyst systems. Accordingly, a need exists for effective techniques for recovering the solubilized noble metal from aqueous process streams produced in the preparation of N-(phosphonomethyl)glycine products by the noble metal-catalyzed oxidation of N-(phosphonomethyl)iminodiacetic acid substrates. The recovered noble metal could be reclaimed and advantageously used in the preparation of fresh catalyst to significantly improve overall economics of the process.

SUMMARY OF THE INVENTION

Among the objects of the present invention, therefore, are the provision of techniques effective for recovering solubilized noble metals from process streams, in particular aqueous process streams generated in the preparation of an N-(phosphonomethyl)glycine product, for example, by the noble metal-catalyzed oxidation of an N-(phosphonomethyl)iminodiacetic acid substrate; the provision of improved processes for the preparation of N-(phosphonomethyl)glycine products by the noble metal-catalyzed oxidation of an N-(phosphonomethyl)iminodiacetic acid substrate in which operational costs are reduced by effective recovery of noble metal solubilized in the reaction product mixture; and the provision of such processes wherein the recovered noble metal may be utilized in the preparation of fresh catalyst.

Briefly, therefore, the present invention is directed to a process for recovering noble metal from an aqueous process stream, including a solubilized noble metal, the aqueous process stream having been generated in a process for making an N-(phosphonomethyl)glycine product by the noble metal-catalyzed oxidation of an N-(phosphonomethyl)iminodiacetic acid substrate. The recovery process includes contacting the aqueous process stream with a noble metal adsorption media to remove at least a portion of the solubilized noble metal therefrom and produce a treated aqueous process stream having a reduced concentration of noble metal and a noble metal adsorption media comprising a noble metal.

The present invention is further directed to a process for making an N-(phosphonomethyl)glycine product. The process includes oxidizing an N-(phosphonomethyl)iminodiacetic acid substrate in an oxidation reactor system in the presence of an oxidation catalyst including a noble metal to produce a reaction product mixture comprising the noble metal catalyst and a reaction product solution comprising N-(phosphonomethyl)glycine product and solubilized noble metal. The N-(phosphonomethyl)glycine product is then precipitated in crystal form from the reaction product solution to produce a product slurry comprising precipitated N-(phosphonomethyl)glycine product crystals and a mother liquor containing the solubilized noble metal. The N-(phosphonomethyl)glycine product crystals are separated from the product slurry to produce an N-(phosphonomethyl)glycine product wet-cake and an aqueous solids-depleted stream containing mother liquor and the noble metal. Finally, at least a portion of the aqueous solids-depleted stream is contacted with a noble metal adsorption media to remove at least a portion of the solubilized noble metal from the aqueous solids-depleted stream and produce a treated aqueous solids-depleted stream having a reduced concentration of noble metal and a noble metal adsorption media comprising a noble metal.

The present invention is further directed to a process for making an N-(phosphonomethyl)glycine product. The process includes oxidizing an N-(phosphonomethyl)iminodiacetic acid substrate in an oxidation reactor system in the presence of an oxidation catalyst including a noble metal to produce a reaction product mixture comprising the noble metal catalyst and a reaction product solution including N-(phosphonomethyl)glycine product and solubilized noble metal. The reaction product solution is concentrated to precipitate the N-(phosphonomethyl)glycine product in crystal form from the reaction product solution to produce an aqueous overhead stream comprising a compound selected from the group of formaldehyde, formic acid and mixtures thereof and a product slurry comprising precipitated N-(phosphonomethyl)glycine product crystals and a mother liquor. The aqueous overhead stream is then contacted with an oxidation catalyst including a noble metal to convert at least a portion of the formic acid and/or formaldehyde to carbon dioxide and water and produce an oxidized overhead stream comprising solubilized noble metal. Finally, at least a portion of the oxidized overhead stream is contacted with a noble metal adsorption media to remove at least a portion of the solubilized noble metal from the oxidized overhead stream and to produce a treated oxidized overhead stream having a reduced concentration of noble metal and a noble metal adsorption media comprising the noble metal.

In one embodiment of the processes described above, the solubilized noble metal removed from the aqueous process stream is in a soluble form and may be in the form of a chelated complex formed with ligands of one or more organic chelating agents selected from the group consisting of N-(phosphonomethyl)glycine, N-(phosphonomethyl)iminodiacetic acid, N-methyl-N-(phosphonomethyl)glycine, N-formyl-N-(phosphonomethyl)glycine, aminomethylphosphonic acid, methylaminomethylphosphonic acid, iminodiacetic acid and/or glycine. In another embodiment, the solubilized noble metal is platinum or palladium. In another embodiment, the noble metal adsorption media is selected from the group consisting of an ion exchange resin, activated carbon and mixtures thereof. In still another embodiment, the noble metal is reclaimed from the noble metal adsorption media by incinerating the noble metal adsorption media to form an ash containing the noble metal, which is then further treated to remove the noble metal from the ash.

The present invention is still further directed to a noble metal adsorption media having a noble metal adsorbed thereon in the form of a noble metal and/or a chelated complex formed with ligands of one or more organic chelating agents including N-(phosphonomethyl)glycine, N-(phosphonomethyl)iminodiacetic acid, N-methyl-N-(phosphonomethyl)glycine, N-formyl-N-(phosphonomethyl)glycine, aminomethylphosphonic acid, methylaminomethylphosphonic acid, iminodiacetic acid and/or glycine. The noble metal adsorption media may further have one or more organic compounds including N-(phosphonomethyl)glycine product, unreacted N-(phosphonomethyl)iminodiacetic acid substrate, N-methyl-N-(phosphonomethyl)glycine (NMG), N-formyl-N-(phosphonomethyl)glycine (NFG), aminomethylphosphonic acid (AMPA), methyl aminomethylphosphonic acid (MAMPA), iminodiacetic acid (IDA) and/or glycine adsorbed on the surface thereof.

Other objects and features of this invention will be in part apparent and in part pointed out hereinafter.

DESCRIPTION OF THE PREFERRED EMBODIMENTS

In accordance with the present invention, effective techniques for the recovery of solubilized noble metals from process streams have been discovered. The techniques have particular application in the recovery of solubilized noble metals from aqueous process streams generated in the preparation of an N-(phosphonomethyl)glycine product, for example, by the noble metal-catalyzed oxidation of an N-(phosphonomethyl)iminodiacetic acid substrate. In general, the recovery techniques include contacting the aqueous process streams containing solubilized noble metal with a noble metal adsorption media, for example, an ion exchange resin, to remove at least a portion of the solubilized noble metal therefrom and produce a treated stream having a reduced concentration of noble metal. The treated stream having a reduced concentration of noble metal may be recycled or purged from the process in accordance with conventional practice. The noble metal removed from the treated stream can be reclaimed from the adsorption media and used in the preparation of fresh catalyst to thereby reduce operational costs and improve overall process economics in the preparation of N-(phosphonomethyl)glycine products.

The techniques for recovery of solubilized noble metal in accordance with the present invention can be applied generally to process streams generated in the noble metal-catalyzed oxidation of a wide variety of reagents in which the noble metal is subject to dissolution or leaching into the oxidation reaction mixture during the course of liquid phase oxidation. For example, the present invention has application in the recovery of solubilized noble metal from process streams emanating from processes for the noble metal-catalyzed oxidation of an N-substituted-N-(phosphonomethyl)glycine substrate (e.g., N-methyl-N-(phosphonomethyl)glycine) to produce N-(phosphonomethyl)glycine as disclosed, for example, by Morgenstern et al. in U.S. Pat. Nos. 6,005,140 and 6,232,494. However, the present invention has particular application in the recovery of solubilized noble metal from aqueous process streams generated in the preparation of an N-(phosphonomethyl)glycine product by noble metal-catalyzed oxidation of an N-(phosphonomethyl)iminodiacetic acid substrate in an aqueous reaction mixture. As will be discussed in greater detail below, the present invention also has particular application in recovery of solubilized noble metal from aqueous process streams resulting from the noble metal-catalyzed oxidation of formaldehyde and/or formic acid, for example, aqueous waste streams generated in the concentration and purification of the N-(phosphonomethyl)glycine product and treated as disclosed, for example, by Smith in U.S. Pat. No. 5,606,107.

Figure 1:
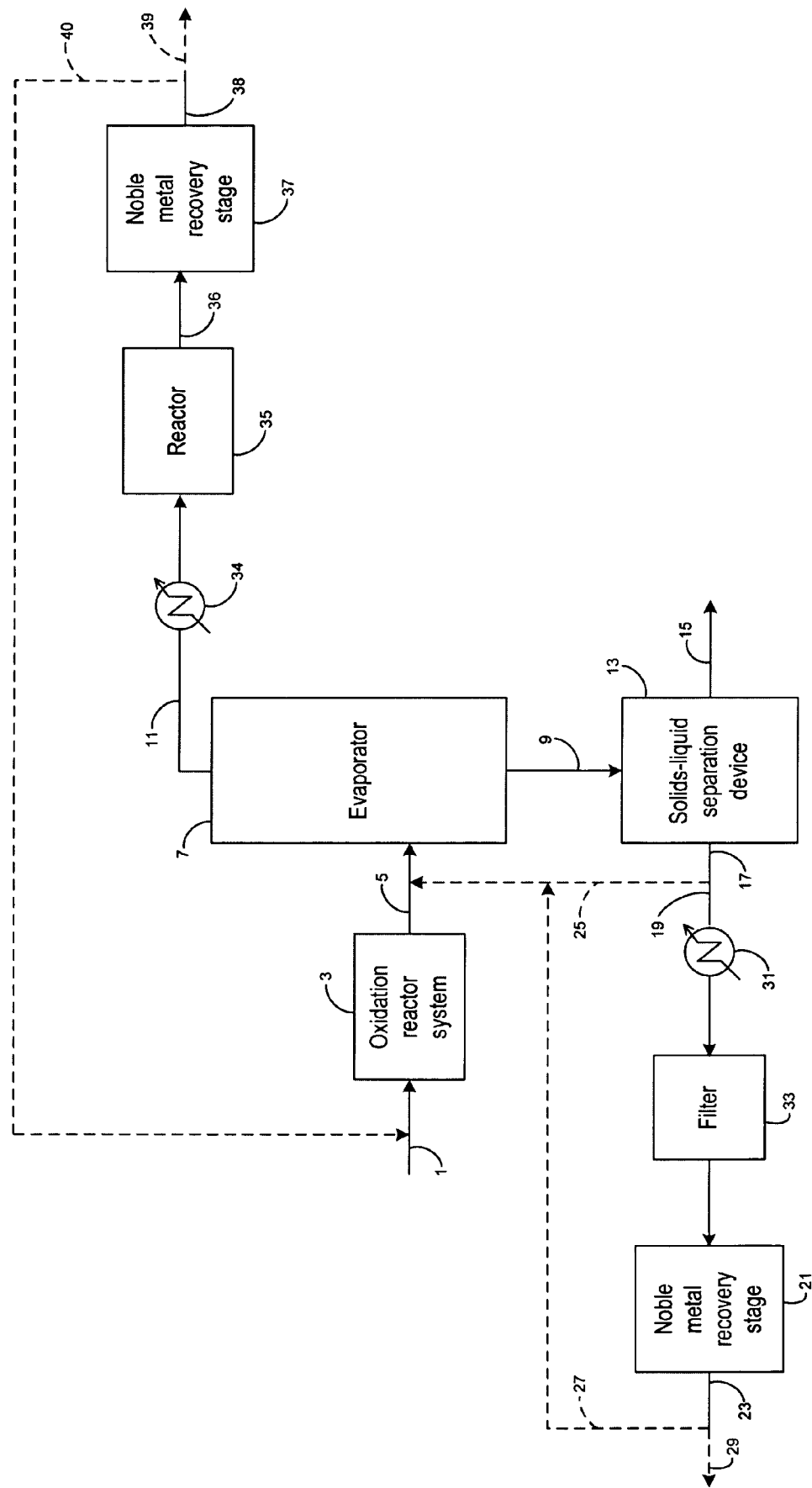
FIG. 1 is a schematic diagram of a process for making N-(phosphonomethyl)glycine product by the noble metal-catalyzed oxidation of an N-(phosphonomethyl)iminodiacetic acid substrate including recovery of solubilized noble metal from aqueous process streams generated.

For the purpose of illustration of some of the preferred embodiments of the present invention, recovery of solubilized noble metal from a process stream will be described in connection with a process for making N-(phosphonomethyl)glycine product by the noble metal-catalyzed oxidation of an N-(phosphonomethyl)iminodiacetic acid substrate as depicted in FIG. 1. FIG. 1 is a schematic diagram of a process for making N-(phosphonomethyl)glycine product by noble metal-catalyzed oxidation of an N-(phosphonomethyl)iminodiacetic acid substrate including recovery of solubilized noble metal from process streams generated in the recovery and purification of the N-(phosphonomethyl)glycine product by concentration of the oxidation product solution.

An aqueous feed stream 1 comprising an N-(phosphonomethyl)iminodiacetic acid substrate is introduced along with an oxygen-containing gas or other oxidizing agent into an oxidation reactor system 3 comprising one or more oxidation reaction zone(s) wherein the N-(phosphonomethyl)iminodiacetic acid substrate is oxidatively cleaved in an aqueous reaction mixture containing a noble metal catalyst to form an oxidation product solution 5 containing the N-(phosphonomethyl)glycine product.

A wide variety of heterogeneous oxidation catalysts comprising one or more noble metal(s) are known for catalyzing the liquid phase oxidation of an N-(phosphonomethyl)iminodiacetic acid substrate to prepare N-(phosphonomethyl)glycine and related compounds and the present invention is generally applicable to processes using any such catalysts. Preferably, the heterogeneous oxidation catalyst employed in the oxidation reaction zone(s) is a bifunctional catalyst comprising one or more noble metal(s) deposited at the surface of a particulate carbon support. In accordance with an especially preferred embodiment, the heterogeneous catalyst used in the liquid phase oxidative cleavage of the N-(phosphonomethyl)iminodiacetic acid substrate is a "deeply reduced" catalyst as described by Ebner et al. in U.S. Pat. No. 6,417,133, by Leiber et al. in U.S. Pat. No. 6,586,621 and by Leiber et al. in U.S. Published Application No. US 2002/0068836 A1 comprising one or more noble metal(s) deposited at the surface of a particulate carbon support and optionally including one or more catalyst surface promoter(s) (e.g., alloyed with the noble metal(s)). By using a deeply reduced noble metal on carbon catalyst in accordance with the referenced patents, leaching of noble metal into the reaction mixture is minimized to lessen the demands placed on the noble metal recovery system in accordance with the present invention.

Suitable noble metals useful in the oxidation of an N-(phosphonomethyl)iminodiacetic acid substrate are selected from the group consisting of platinum (Pt), palladium (Pd), ruthenium (Ru), rhodium (Rh), iridium (Ir), silver (Ag), osmium (Os), gold (Au) and mixtures thereof. In general, platinum and palladium are more preferred, and platinum is most preferred. Because platinum is currently the most preferred noble metal, the following discussion regarding recovery of solubilized noble metal will be directed primarily to embodiments using platinum. It should be understood, however, that the present invention is generally applicable to the recovery of the other noble metals and combinations thereof. Likewise, suitable optional metal surface promoters are selected from the group consisting of tin (Sn), cadmium (Cd), magnesium (Mg), manganese (Mn), nickel (Ni), aluminum (Al), cobalt (Co), bismuth (Bi), lead (Pb), titanium (Ti), antimony (Sb), selenium (Se), iron (Fe), rhenium (Re), zinc (Zn) cerium (Ce), zirconium (Zr), tellurium (Te), germanium (Ge) and mixtures thereof. Preferably, the promoter is selected from the group consisting of bismuth, iron, tin, tellurium and cobalt. In one particularly preferred embodiment, the promoter is iron. Catalysts comprising iron generally are most preferred because they tend to have the greatest activity and stability with respect to formaldehyde and formic acid oxidation. The selection of carbon supports, noble metal(s) and optional surface promoter combinations and alloys and processes for preparation of the preferred bifunctional catalysts are described by Ebner et al. in U.S. Pat. No. 6,417,133, Leiber et al. in U.S. Pat. No. 6,586,621, Leiber in U.S. Pat. Nos. 6,927,304 and 6,956,005 and by Haupfear et al. in U.S. Published Application No. US 2002/0068836 A1. However, as noted above, it should be understood that the advantages provided by the present invention are applicable with respect to a wide assortment of commercially available noble metal on carbon catalysts.

As now recognized in the art, the liquid phase oxidation of N-(phosphonomethyl)iminodiacetic acid substrates may be carried out in a batch, a semi-batch or a continuous reactor system containing one or more oxidation reaction zones. The oxidation reaction zone(s) may be suitably provided by various reactor configurations, including those that have back-mixed characteristics, in the liquid phase and optionally in the gas phase as well, and those that have plug flow characteristics. Suitable reactor configurations having back-mixed characteristics include, for example, stirred tank reactors, ejector nozzle loop reactors (also known as venturi-loop reactors) and fluidized bed reactors. Suitable reactor configurations having plug flow characteristics include those having a packed or fixed catalyst bed (e.g., trickle bed reactors and packed bubble column reactors) and bubble slurry column reactors. Fluidized bed reactors may also be operated in a manner exhibiting plug flow characteristics. The configuration of the oxidation reactor system and the number of oxidation reaction zones is not critical to the practice of the present invention. However, it is preferred that the oxidation reactor system employed be adapted for use of a particulate noble metal on carbon catalyst suspended in the aqueous reaction mixture and include a filter to separate the particulate catalyst from the aqueous reaction mixture to provide the oxidation product solution 5 substantially free of the oxidation catalyst and comprising the N-(phosphonomethyl)glycine product. The separated catalyst can be recycled and reintroduced into the oxidation reaction zone(s).

Likewise, suitable conditions, including temperature and pressure maintained in the oxidation reaction zone(s), reagent concentrations, catalyst loading or concentration, reaction time, oxygen feed rates, etc., suitable for liquid phase oxidative cleavage of a carboxymethyl substituent from an N-(phosphonomethyl)iminodiacetic acid substrate in an aqueous reaction mixture containing a noble metal catalyst are well-known to those skilled in the art and the selection of these process parameters is not critical to the practice of the present invention. The temperature within the oxidation reaction zone(s) is preferably maintained sufficiently high with respect to the concentration of the N-(phosphonomethyl)glycine product such that essentially all the N-(phosphonomethyl)glycine product in the aqueous reaction mixture remains dissolved so that the suspended particulate catalyst can be readily recovered for re-use, for example, by filtration. The pressure is generally maintained sufficient to prevent the aqueous reaction mixture from boiling and is adequate to cause molecular oxygen from an oxygen-containing gas to dissolve into the reaction mixture at a rate sufficient such that oxidation of the N-(phosphonomethyl)iminodiacetic acid substrate is not limited due to an inadequate oxygen supply.

Suitable oxidation reactor systems and oxidation reaction conditions for liquid phase catalytic oxidation of an N-(phosphonomethyl)iminodiacetic acid substrate are described, for example, by Ebner et al. in U.S. Pat. No. 6,417,133, by Leiber et al. in U.S. Pat. No. 6,586,621, by Leiber in U.S. Pat. Nos. 6,927,304 and 6,956,005 and by Haupfear et al. in U.S. Publication No. US 2002/0068836 A1.

The oxidation product solution 5 discharged from the oxidation reactor system 3 contains the N-(phosphonomethyl) glycine product and also typically contains unreacted substrate and various by-products of the oxidation reaction such as those noted above as well as any impurities present in the feed materials. In addition, the oxidation product solution contains solubilized noble metal leached from the catalyst in the oxidation reaction zone(s). The solubilized noble metal may be present in one or more various forms including solubilized noble metal ions and colloids. It is presently believed that a portion of the solubilized noble metal component may be present in chelate complexes formed with ligands of one or more various organic chelating agents present in the oxidation product solution, including the N-(phosphonomethyl)glycine product, unreacted N-(phosphonomethyl)iminodiacetic acid substrate, N-methyl-N-(phosphonomethyl)glycine (NMG), N-formyl-N-(phosphonomethyl)glycine (NFG), aminomethylphosphonic acid (AMPA), methyl aminomethylphosphonic acid (MAMPA), iminodiacetic acid (IDA) and glycine.

Commercial considerations often dictate that the concentration of the N-(phosphonomethyl)glycine product in the commercially sold mixtures be significantly greater than the concentration in the oxidation product solution 5 as typically formed in the oxidation reactor system 3, particularly where the N-(phosphonomethyl)glycine product is being stored or shipped for agricultural applications. For example, when a heterogeneous noble metal on carbon catalyst is used for the liquid phase oxidation of N-(phosphonomethyl)iminodiacetic acid to make N-(phosphonomethyl)glycine, it is typically preferred to maintain a maximum concentration of the N-(phosphonomethyl)glycine product in the oxidation product solution of no greater than about 9% by weight in order to keep the product solubilized, although higher concentrations in excess of 9% and even up to about 12% by weight or higher may be utilized at higher reaction temperatures. Sometimes, however, it is desirable for the commercially sold mixtures to have an N-(phosphonomethyl)glycine concentration that is significantly greater. Thus, after the N-(phosphonomethyl)glycine product has been formed and separated from the catalyst in the oxidation reaction mixture, the oxidation product solution may be concentrated and the product separated from the various impurities and other components contained therein.

Accordingly, as shown in FIG. 1, the oxidation product solution 5 withdrawn from the reactor system 3 is introduced into a crystallizer stage comprising an evaporator 7 and concentrated to produce a crystallization product slurry 9 comprising precipitated N-(phosphonomethyl)glycine product crystals and residual reaction solution or mother liquor and an evaporator overhead stream 11. The evaporator 7 may be of any suitable design and may be operated substantially adiabatically or comprise a non-adiabatic, heat-driven evaporative crystallizer.

The crystallization product slurry 9 comprising precipitated crystalline N-(phosphonomethyl)glycine product and mother liquor is removed from the evaporator and introduced into a solids-liquid separation device 13. Suitable solids-liquid separation devices include, for example, vacuum drums, vacuum table filters and/or centrifuges. In a particularly preferred embodiment, N-(phosphonomethyl)glycine product crystals are separated from the mother liquor in the crystallization product slurry 9 by centrifugation, for example in a solid bowl centrifuge, basket centrifuge or bank of basket centrifuges, to produce an N-(phosphonomethyl)glycine wet-cake product 15 and an aqueous solids-depleted stream 17 (e.g., centrate) comprising mother liquor.

Preferably, the N-(phosphonomethyl)glycine wet-cake product 15 has a solids content of at least about 75% by weight or more, for example, from about 80% to about 99% by weight, typically from about 85% to about 95% by weight. The solids-depleted stream 17 comprises mother liquor and contains soluble components of the oxidation product solution not precipitated or otherwise entrapped or incorporated in the N-(phosphonomethyl)glycine product crystals formed in the crystallization stage. These soluble components include solubilized noble metal in the form of ions or colloids and/or sequestered in organic chelates as described above. As used herein, solubilized noble metal refers to any of these various forms.

In accordance with the present invention, at least a portion 19 of the solids-depleted stream 17 is introduced into a noble metal recovery stage 21 and contacted with a noble metal adsorption media therein to remove at least a portion of the solubilized noble metal content and produce a treated solids-depleted stream 23 having a reduced concentration of solubilized noble metal. Any remaining portion 25 of the solids-depleted stream 17 may be recycled, for example, to evaporator 7 in the crystallization stage and/or purged from the process. At least a portion of the treated solids-depleted stream 23 may likewise be recycled, for example, to evaporator 7 in the crystallization stage and/or a portion 29 may be purged from the process.

The noble metal adsorption media should be selected so as to be capable of adsorbing at least a portion of the solubilized noble metal load in the presence of the other components present and under the other relevant conditions prevailing in the stream to be treated that might affect noble metal adsorption, including pH. In accordance with the present invention, noble metal adsorption media have been identified that effectively remove solubilized noble metals, particularly platinum, present in the concentrations typically encountered in acidic aqueous process streams such as in solids-depleted stream 17 generated in the preparation of an N-(phosphonomethyl)glycine product. Generally, the noble metal adsorption media may be in the form of one or more carbonaceous material(s), one or more ion exchange resin(s), or a combination thereof.

In one embodiment of the present invention, the aqueous process stream to be treated is contacted with noble metal adsorption media comprising a carbonaceous material, such as activated carbon. Suitable activated carbon media for use in the practice of the present invention are commercially available, and include, for example, Calgon Activated Carbon CPG 12X40 from Calgon Carbon Corporation (Pittsburgh, Pa.). In general, suitable activated carbon media may have an average particle size of from about 40 µm to about 4000 µm, typically from about 250 µm to about 2000 µm. In one embodiment, the activated carbon media has an average particle size of from about 300 µm to about 2000 µm, preferably from about 420 µm to about 1680 µm.

Preferably, the noble metal adsorption media comprises an ion exchange resin or a mixture of ion exchange resins. Broadly described, ion exchange is the reversible interchange of ions between a solid and liquid in which there is no permanent change in the structure of the ion exchange material. In the practice of the present invention, suitable ion exchange resins may be selected from the group consisting of strong base anion exchange resins, weak base anion exchange resins, strong acid cation exchange resins, weak acid cation exchange resins, chelating resins, and mixtures thereof. Preferably, the ion exchange resin has a functional group selected from the group consisting of thiouronium, isothiouronium, thiol, α-hydroxy thiol, iminodiacetate, quaternary amine, aminophosphonic and mixtures thereof. In accordance with one particularly preferred embodiment, the ion exchange resin possesses a thiouronium functional group. Suitable ion exchange resins are commercially available, and include, for example, Dowex 21XLT, Dowex M43 and Dowex 21K Cl from Dow (Midland, Mich.), Graver 905, Graver 934, Graver 962, and Graver 981 from Graver (Newark, Del.), Smopex 105, Smopex 110, Smopex 112, and Smopex 113 from Johnson Matthey (West Deptford, N.J.), Purolite A-501P, Purolite A-600, Purolite A-830W, Purolite S-920, and Purolite S-950 from Purolite (Bala Cynwyd, Pa.), ResinTech SIR 200, ResinTech SIR 300, ResinTech SIR 400, ResinTech SIR 500 and ResinTech SBG-1 from ResinTech (West Berlin, N.J.), and Ionac SR-3 from Sybron (Birmingham, N.J.). In general, suitable ion exchange resins may have an average particle size of from about 150 µm to about 2000 µm. In one preferred embodiment, the ion exchange resin has an average particle size of from about 300 µm to about 1200 µm. The average particle size of the ion exchange resin may be measured by various analytical methods generally known in the art including, for example, ASTM E-11-61.

The particular construction and configuration of noble metal recovery stage 21 is not critical in the practice of the present invention. Typically, the noble metal recovery stage comprises a porous bed of the noble metal adsorption media suitably contained within a vessel (e.g., a cylindrical column). The vessel used to contain the noble metal adsorption media is preferably constructed of materials that exhibit adequate corrosion resistance with respect to the composition of the stream to be treated. For example, in treating aqueous process streams generated in the preparation of an N-(phosphonomethyl)glycine product, a stainless steel vessel is suitable for containing the noble metal adsorption media in the recovery stage. In accordance with the present invention, noble metal recovery stage 21 may contain two or more ion exchange resins or other noble metal adsorption media as described above, each particularly adapted for effectively adsorbing one or more of the various forms of solubilized noble metal(s) present in the process stream to be treated. Multiple noble metal adsorption media may be mixed in a single bed or placed in separate beds housed in a single or multiple separate vessels or columns. The vessel may include one or more support screens for supporting the bed of noble metal adsorption media within the vessel and one or more liquid distributors to promote more uniform flow through the noble metal adsorption media. When an ion exchange resin is employed, the vessel is typically only partially filled with the ion exchange media (e.g., between one-half and two-thirds of the vessel volume) to accommodate expansion or swelling of the media due to hydration during use.

Noble metal recovery stage 21 may be operated in a batch, semi-batch or continuous mode. Preferably, the noble metal recovery stage is operated continuously and comprises a suitably adapted flow-through vessel provided with an inlet for introducing the process stream to be treated and an outlet for discharging the treated stream.

The portion 19 of solids-depleted stream 17 contacted with the noble metal adsorption media is desirably maintained at a temperature sufficient such that soluble components such as the N-(phosphonomethyl)glycine product remain in solution so as to avoid precipitation of the product and clogging of noble metal recovery stage 21. Typically, the temperature of the solids-depleted stream 19 contacted with the noble metal adsorption media is maintained at a temperature of at least about 25° C., preferably from about 60 to about 95° C., and more preferably from about 75 to about 90° C. As shown in FIG. 1, the portion 19 of the solids-depleted stream to be introduced into the noble metal recovery stage may be passed through in-line heater 31 to maintain the temperature of the stream as desired. Alternatively, heat may be supplied to the process stream as it is treated in noble metal recovery stage 21. To protect the noble metal adsorption media from excessive contact with solids (e.g., N-(phosphonomethyl)glycine product crystals) that may be present in the solids-depleted stream 17 from time to time and during process upsets, a pre-filter 33 upstream of the noble metal recovery stage 21 may be provided. In one embodiment, pre-filter 33 may comprise a bag filter.

The quantity of adsorption media utilized and the size of the vessel used to contain the media in noble metal recovery stage 21 can be readily determined experimentally and is dependent upon a variety of factors including the volume or flow rate of the process stream to be treated, the concentration of the solubilized noble metal and overall composition of the process stream to be treated, the effectiveness of the adsorption media and the desired level of removal.

The concentration of solubilized noble metal in the process streams treated in accordance with the present invention may vary considerably depending upon, among other things, the operating conditions in the oxidation reactor system 3 and the particular noble metal catalyst used to catalyze the oxidation reaction. Generally, the concentration of the solubilized noble metal in the process stream introduced into the noble metal recovery stage is at least about 0.1 ppm. Typically, the process stream to be treated has a solubilized noble metal content of from about 0.1 ppm to about 1000 ppm, from about 0.1 ppm to about 100 ppm and more typically from about 1 ppm to about 50 ppm. In one embodiment, the concentration of solubilized noble metal in the process stream to be treated is from about 1 ppm to about 20 ppm. In another embodiment, the concentration of solubilized noble metal in the process stream to be treated is from about 2 ppm to about 8 ppm or even about 3 ppm to about 6 ppm.

Generally, the noble metal recovery stage 21 is constructed and operated such that at least about 20 percent of the solubilized noble metal content in the process stream to be treated is removed by the noble metal adsorption media. Typically, from about 20 to about 99 percent of the solubilized noble metal loading may be removed. In one embodiment, from about 60 to about 90 percent and in another embodiment, from about 60 to about 85 percent of the solubilized noble metal is removed in the noble metal recovery stage. The treated process stream generally has less than about 80 ppm solubilized noble metal, typically less than 30 ppm solubilized noble metal or even less than 15 ppm solubilized noble metal. In one embodiment, the treated process stream may have less than about 10 ppm solubilized noble metal. In another embodiment, the treated process stream has a concentration of solubilized noble metal of from about 0.1 ppm to about 5 ppm or even from about 1 ppm to about 3 ppm.

Noble metal recovery stage 21 is constructed and operated in a manner such that the process stream to be treated is contacted with the noble metal adsorption media for a sufficient period to remove at least a portion of the solubilized noble metal(s) in the stream and attain the desired level of removal in the treated stream. The contact period may vary considerably in the practice of the present invention in view of the various considerations noted herein. In the continuous operation of the noble metal recovery stage, the contact period may be described in terms of bed volumes per unit time defined as the volumetric flow rate of the process stream passing through the bed of noble metal adsorption media divided by the volume of the bed. The requisite contact period in terms of the bed volumes per unit time for a particular process stream to be treated and a selected noble metal adsorption media may be determined by those skilled in the art through routine experimentation. For example, a sample of the process stream to be treated may be passed through a fixed volume of the selected noble metal adsorption media at varying volumetric flow rates. The inlet concentration of solubilized noble metal in the process stream to be treated prior to contact with the noble metal adsorption media, and the outlet concentration in the treated stream after contact are measured to determine the amount of noble metal removed from the process stream. The concentration of noble metal in the process stream and treated stream may be measured by various analytical methods generally known in the art including, for example, Inductively Coupled Plasma Mass Spectrometry (ICP-MS), Inductively Coupled Plasma-Optical Emission Spectrometry (ICP-OES) and Atomic Absorbance Spectrometry (AA). ICP-MS works particularly well in determining the solubilized noble metal concentration in streams containing organic species. Once the maximum flow rate at which the desired level of removal can be attained is determined, the requisite contact time in terms of bed volume per unit time can be calculated and used to size a suitable noble metal recovery stage for treating the process stream. Generally, in view of the various considerations noted above, the contact time of the process stream with the noble metal adsorption media in a continuous noble metal recovery stage is from about 1 to about 60 bed volumes per hour, typically from about 2 to about 20 bed volumes per hour. In accordance with one preferred embodiment, the noble metal recovery stage is sized and configured so as to attain the desired level of solubilized noble metal removal in a contact time of from about 3 to about 8 bed volumes per hour.

The effectiveness of ion exchange resins and other noble metal adsorption media in terms of removal efficiency typically deteriorates with use. In accordance with the present invention, noble metal adsorption and removal efficiency in the noble metal recovery stage can be monitored to determine when the adsorption media should be replaced. In one embodiment, the noble metal adsorption media may be replaced when the noble metal adsorption capacity of the material is completely spent as determined, for example, when the solubilized noble metal concentration in the treated process stream exiting the noble metal recovery stage is roughly equivalent to the concentration of solubilized noble metal in the process stream to be treated. Typically, however, economic considerations may dictate that the noble metal adsorption media be replaced prior to becoming completely spent. For a particular system, those skilled in the art will be readily able to determine when continued use of noble metal adsorption media is no longer economically viable in view of increased noble metal losses and the capital expenditure necessary for replacement.

The spent media removed from the noble metal recovery stage comprises adsorbed noble metal, and may include noble metal present in chelate complexes formed with the various organic ligands in the oxidation product solution as described above. The adsorbed noble metal component of the spent adsorption media may be recovered by conventional means. For example, the spent adsorption media may be contacted with a washing solution (e.g. a strong acid) capable of removing the noble metal component from the adsorption media to cause the noble metal component to be transferred from the ion exchange resin to the washing solution from which the noble metal can be extracted using well-known techniques. Typically, the adsorbed noble metal component of the spent adsorption media may be recovered by incinerating the media to produce an ash composition from which the noble metal can be extracted using well-known techniques. The reclaimed noble metal may then be advantageously used in preparing fresh noble metal catalyst for use in the oxidation of N-(phosphonomethyl)iminodiacetic acid substrate.

In another embodiment of the present invention, a noble metal adsorption media is used to recover solubilized noble metal from aqueous process streams resulting from noble metal-catalyzed oxidation of formaldehyde and/or formic acid, for example, aqueous waste streams generated in the concentration and purification of the N-(phosphonomethyl) glycine product and treated as disclosed, for example, by Smith in U.S. Pat. No. 5,606,107.

The evaporator overhead stream 11 shown in FIG. 1 typically contains unreacted formaldehyde and/or formic acid. The presence of formaldehyde or formic acid may render this stream potentially toxic and unsuitable for discharge or recycle to the process for preparing the N-(phosphonomethyl)glycine product. As disclosed by Smith in U.S. Pat. No. 5,606,107, process waste streams having an undesirably high level of formaldehyde and/or formic acid such as evaporator overhead stream 11 may be treated by catalytically oxidizing the formaldehyde and/or formic acid using a noble metal catalyst to convert the formaldehyde and formic acid to environmentally benign carbon dioxide and water. The noble metal catalyst used to oxidize the formaldehyde and/or formic acid in the evaporator overhead stream 11 may suitably be the same type of catalyst described above for oxidation of an N-(phosphonomethyl)iminodiacetic acid substrate.

As shown in FIG. 1, evaporator overhead stream 11 may be at least partially condensed in condenser 34 and the resulting condensate introduced into a reactor 35 in which at least a portion of the formaldehyde and/or formic acid load present in the condensate is oxidized to carbon dioxide and water in the presence of a noble metal catalyst to produce oxidized overhead stream 36. Noble metal-catalyzed oxidation of the formaldehyde and/or formic acid in the evaporator overhead condensate, may result in solubilized noble metal in the oxidized overhead stream 36. According to the present invention, the solubilized noble metal may be recovered by contacting at least a portion of the oxidized overhead stream 36 with a noble metal adsorption media in a noble metal recovery stage 37 using the techniques discussed in detail above, to produce a treated overhead stream 38. A portion or all of treated overhead stream 38 may be recycled, for example, to the oxidation reactor system 3 as a source of make-up water. Alternatively, a portion 39 or all of the treated overhead stream 38 may be purged from the process.

Although the noble metal recovery techniques of the present invention are illustrated in FIG. 1 for the treatment of solids-depleted stream 17 and/or overhead stream 11 resulting from the concentration and purification of an N-(phosphonomethyl)glycine product solution, it should be recognized that such techniques may be applied to treat other aqueous process streams generated in the production of an N-(phosphonomethyl)glycine product.

The following examples are simply intended to further illustrate and explain the present invention. The invention, therefore, should not be limited to any of the details in these examples.

Example 1

Removal of Solubilized Platinum from an Aqueous Process Stream Using Various Ion Exchange Resins Samples of an aqueous process stream containing solubilized platinum were contacted with various ion exchange resins in a laboratory-scale, batch-operated noble metal recovery stage to evaluate their effectiveness in removing the solubilized platinum. The aqueous process stream utilized in this example was filtered, solids-depleted stream 17 (i.e., centrate) obtained from the preparation of N-(phosphonomethyl)glycine by platinum on carbon catalyzed oxidation of N-(phosphonomethyl)iminodiacetic acid in accordance with a process similar to that shown and described in FIG. 1. In addition to the solubilized platinum and N-(phosphonomethyl)glycine product components, such centrates typically also contain low levels of unreacted N-(phosphonomethyl) iminodiacetic acid, formaldehyde, formic acid, N-methyl-N-(phosphonomethyl)glycine (NMG), N-formyl-N-(phosphonomethyl)glycine (NFG), aminomethylphosphonic acid (AMPA), methyl aminomethylphosphonic acid (MAMPA), iminodiacetic acid (IDA) and/or glycine.

For each experimental run, an aliquot of the solids-depleted centrate solution to be treated was weighed out in a laboratory beaker. A sample of ion exchange resin as received was then weighed out as a percentage of the weight of the centrate aliquot. The "resin loading" defined as the weight of the ion exchange resin divided by the weight of the centrate sample to be treated multiplied by 100 is reported in Table 1 below. As reported in Table 1, numerous experiments were conducted using a variety of ion exchange resins at various resin loadings. Some experiments were performed with a single resin type, while others were performed using a mixture of more than one resin type.

In each experiment, the resin sample was added to the centrate solution aliquot in the beaker and, unless noted otherwise, the mixture was stirred for one hour at room temperature. At the end of the treatment time, the mixture of resin and centrate solution was passed through a 0.5 μm filter to remove the resin. The concentration of solubilized platinum in the centrate solution sample was analyzed both before and after treatment with the ion exchange resin using Inductively Coupled Plasma Mass Spectroscopy (ICP-MS). The calculated percentage of solubilized platinum removed from the centrate solution sample by the ion exchange resin is reported in Table 1.

As shown in Table 1, a substantial portion of the platinum was successfully removed from the centrate solution using a number of different ion exchange resins.

Example 2

Removal of Solubilized Platinum Complexes from Aqueous Solutions Using an Ion Exchange Resin Samples of various aqueous solutions containing a solubilized platinum complex listed in Table 2 were contacted with various ion exchange resins in a laboratory-scale, batch-operated noble metal recovery stage to evaluate their effectiveness in removing platinum from the solution containing a solubilized platinum complex.

For each experiment, 0.5 grams of the ion exchange resin sample was added to 100 mL of aqueous solution containing an initial concentration of solubilized platinum complex. In two experimental runs, the aqueous solution was filtered, solids-depleted stream 17 (i.e., centrate) obtained from the preparation of N-(phosphonomethyl)glycine by platinum on carbon catalyzed oxidation of N-(phosphonomethyl)iminodiacetic acid in accordance with a process similar to that shown and described in FIG. 1. The resulting mixture was stirred for one hour at a temperature of 25° C. At the end of the stirring time, the mixture of resin and aqueous solution containing the solubilized platinum complex was passed through

TABLE 1

Removal of Solubilized Platinum from Solids-Depleted Centrate

| Resin | Functionality | Percent Platinum Removal Measured for Various Resin Loading Percentages Ranging from 0.02 to 1.0 percent | | | | |
|---|---|---|---|---|---|---|
| | | 0.02 | 0.10 | 0.20 | 0.50 | 1.0 |
| Graver 934 | anion exchange | 64.6 | 75.0 | — | 83.3 | — |
| Graver 934 | anion exchange | 41.2 | 52.9 | — | 71.5 | — |
| Graver 934 stirred for 3 hr | anion exchange | 35.3 | 41.2 | — | 55.9 | — |
| Graver 934 | anion exchange | — | — | — | — | 70.8 |
| Graver 934 | anion exchange | — | — | — | — | 79.2 |
| Graver 934 at 60° C. | anion exchange | — | — | — | 75.0 | — |
| Graver 905 | anion exchange, Cl | 70.8 | 70.8 | — | 68.8 | — |
| Graver 962 | Zeolite | 20.7 | 37.9 | — | 44.8 | — |
| Graver 981 | anion exchange, Cl | 37.9 | 31.0 | — | 51.7 | — |
| Ionac SR-3 | isothiouronium(chelating) | 47.9 | 54.2 | — | 58.3 | — |
| Dowex 21K | anion (quaternary amine) | 20.7 | 41.4 | — | 44.8 | — |
| SIR-200 | Thiol | 17.6 | 38.2 | — | 50.0 | — |
| SIR-300 | iminodiacetate, Na | 32.4 | 38.2 | — | 52.9 | — |
| SIR-400 | isothiouronium(chelating) | 44.1 | 50.0 | — | 75.3 | — |
| SIR-400 stirred for 3 hr | isothiouronium(chelating) | 19.2 | 46.2 | — | 50.0 | — |
| SIR-400 | isothiouronium(chelating) | — | — | — | — | 50.0 |
| SIR-400 | isothiouronium(chelating) | — | — | — | — | 50.0 |
| SIR-400 at 60° C. | isothiouronium(chelating) | — | — | — | 70.8 | — |
| SIR-500 | aminophosphonic | 38.2 | 32.4 | — | 38.2 | — |
| Purolite S-920 | thiouronium(chelating) | 41.2 | 47.1 | — | 61.8 | — |
| Purolite S-950 | aminophosphonic | 44.1 | 44.1 | — | 50.0 | — |
| Smopex 110 | isothiouronium | 52.9 | 55.9 | — | 55.9 | — |
| Smopex 112 | a-hydroxythiol | 7.1 | 10.7 | — | 32.1 | — |
| Amberlyst 15W | sulfonic acid | 0.0 | 0.0 | — | 0.0 | — |
| 50% SIR-400/ 50% Graver 934 | chelating/anion | — | — | — | — | 75 |
| 50% SIR-400/ 50% Graver 934 | chelating/anion | — | — | — | — | 75 |
| 50% SIR-400/ 50% Dowex 21XLT | chelating/anion | — | — | 51.7 | — | — |
| | | — | — | 20.7 | — | — |
| 50% Graver 934/ 50% Dowex 21XLT | anion/anion | — | — | 55.2 | — | — |
| | | — | — | 51.7 | — | — |
| Purolite A-501P | Colloidal | 33.3 | 38.1 | — | 42.9 | — |
| Purolite A-600 | Colloidal | 10.6 | 33.1 | — | 69.6 | — |
| Purolite A-830W | Colloidal | 8.0 | 24.3 | — | 44.9 | — | a 0.5 µm filter to remove the resin from the aqueous solution containing the solubilized platinum complex.

The concentration of platinum in the solution containing solubilized platinum complex was analyzed both before and after treatment with the ion exchange resin using Inductively Coupled Plasma Mass Spectroscopy (ICP-MS). The calculated percentage of platinum removed from the solution by the ion exchange resin is reported on a platinum basis in Table 2.

As shown in Table 2, a substantial portion of the platinum in many of the solutions containing a solubilized platinum complex was successfully removed from the solution using a number of different ion exchange resins.

TABLE 2

Removal of Solubilized Platinum Complexes Using Ion Exchange Resins

| Complex | Resin | Initial Pt Concentration, ppm | Final Pt Concentration, ppm | Pt adsorbed, ppm | % PT Removed |
|---|---|---|---|---|---|
| Pt-Glyphosate | Purolite S-920 | 2.9 | 2.1 | 0.8 | 27.6 |
| | SIR-500 | 2.9 | 2.5 | 0.4 | 13.8 |
| | Dowex 21XLT | 2.9 | 2.5 | 0.4 | 13.8 |
| | SIR-400 | 3.1 | 2.3 | 0.8 | 25.8 |
| | Dowex M-43 | 3.1 | 2.2 | 0.9 | 29.0 |
| Pt-AMPA | Purolite S-920 | 4.2 | 4.7 | −0.5 | 0 |
| | SIR-500 | 4.2 | 5.7 | −1.5 | 0 |
| | Dowex 21XLT | 4.2 | 4.9 | −0.7 | 0 |
| | SIR-400 | 4.2 | 5.4 | −1.2 | 0 |
| | Dowex M-43 | 4.2 | 4.1 | 0.1 | 2.4 |
| $PtCl_4$ | Purolite S-920 | 5.0 | <0.1 | 4.9 | 98.0 |
| | SIR-500 | 5.0 | <0.1 | 4.9 | 98.0 |
| | Dowex 21XLT | 5.0 | <0.1 | 4.9 | 98.0 |
| | SIR-400 | 5.0 | <0.1 | 4.9 | 98.0 |
| | Dowex M-43 | 5.0 | 4.7 | 0.3 | 6.0 |
| $PtCl_6$ | Purolite S-920 | 5.7 | <0.1 | 5.6 | 98.2 |
| | SIR-500 | 5.7 | <0.1 | 5.6 | 98.2 |
| | Dowex 21XLT | 5.7 | <0.1 | 5.6 | 98.2 |
| | SIR-400 | 5.7 | <0.1 | 5.6 | 98.2 |
| | Dowex M-43 | 5.7 | 5.9 | −0.2 | 0 |
| Pt-AMPA | Dowex M43 | 4.7 | 5.3 | −0.6 | 0 |
| | Dowex 21K XLT | 4.7 | 5.0 | −0.3 | 0 |
| | SIR 400 | 4.7 | 5.4 | −0.7 | 0 |
| | Purolite S-920 | 4.7 | 5.5 | −0.8 | 0 |
| | SIR 500 | 4.7 | 5.4 | −0.7 | 0 |
| | Dowex M-43 | 4.7 | 5.4 | −0.7 | 0 |
| | SIR 400 | 4.7 | 5.6 | −0.9 | 0 |
| Solids-depleted Stream 17 Pt Complexes | Smopex 105 | 4.0 | 1.3 | 2.7 | 67.5 |
| | Smopex 112 | 4.0 | 1.4 | 2.6 | 65.0 |
| | Smopex 113 | 4.0 | 2.4 | 1.6 | 40.0 |
| | Smopex 105 | 4.3 | 1.8 | 2.5 | 58.1 |
| | Smopex 112 | 4.3 | 1.9 | 2.4 | 55.8 |
| | Smopex 113 | 4.3 | 2.9 | 1.4 | 32.6 |
| Pt-Glycine | Dowex M43 | 3.1 | 3.4 | −0.3 | 0 |
| | Dowex 21K XLT | 3.1 | 3.3 | −0.2 | 0 |
| | SIR 400 | 3.1 | 3.7 | −0.6 | 0 |
| | SIR 500 | 3.1 | 0.7 | 2.4 | 77.4 |
| | Purolite S-920 | 3.1 | 3.7 | −0.6 | 0 |
| Pt-NMG | Dowex M-43 | 3.1 | 1.8 | 1.3 | 41.9 |
| | Dowex 21XLT | 3.1 | 1.1 | 2.0 | 64.5 |
| | SIR-400 | 3.1 | 2.3 | 0.8 | 25.8 |
| | SIR-500 | 3.1 | 3.1 | 0 | 0 |
| | Purolite S-920 | 3.1 | 1.8 | 1.3 | 41.9 |

Example 3

Removal of Solubilized Platinum from an Aqueous Process Stream Using an Ion Exchange Resin Samples of an aqueous process stream containing solubilized platinum were contacted with various ion exchange resins in a laboratory-scale, continuously-operated noble metal recovery stage comprising a flow through ion exchange column to evaluate their effectiveness in removing the solubilized platinum. The aqueous process stream utilized in this example was filtered solids-depleted stream 17 (i.e., centrate) obtained from the preparation of N-(phosphonomethyl)glycine by platinum on carbon catalyzed oxidation of N-(phosphonomethyl)iminodiacetic acid in accordance with a process similar to that shown and described in FIG. 1. In addition to the solubilized platinum and N-(phosphonomethyl)glycine product components, such centrates typically also contain low levels of unreacted N-(phosphonomethyl)iminodiacetic acid, formaldehyde, formic acid, N-methyl-N-(phosphonomethyl)glycine (NMG), N-formyl-N-(phosphonomethyl)glycine (NFG), aminomethylphosphonic acid (AMPA), methyl aminomethylphosphonic acid (MAMPA), iminodiacetic acid (IDA) and/or glycine.

Tests were conducted by passing solids-depleted process solution over the ion exchange resin being tested in a cylindrical glass column. The liquid flow rates of the solution ranged from about 1.4 BV/hr to about 9 BV/hr (bed volume per hour). The concentration of solubilized platinum in the centrate solution in the inlet to the column and the effluent from the column was analyzed using Inductively Coupled Plasma Mass Spectroscopy (ICP-MS). The concentration of solubilized platinum in the inlet to the column and the effluent from the column and the calculated percentage of solubilized platinum removed from the centrate solution sample by the ion exchange resin are reported in Table 3.

As shown in Table 3, a substantial portion of the platinum was successfully removed from the centrate solution using a number of different ion exchange resins.

Example 4

Removal of Solubilized Platinum from an Aqueous Process Stream Using an Ion Exchange Resin A test was conducted to recover solubilized platinum from the solids-depleted stream 17 (i.e., centrate) obtained from

TABLE 3

Removal of Solubilized Platinum from Solids-Depleted Centrate

| Resin | Resin gms | Flow mL/min | Bed Volume cm³ | BV/hr | Inlet ppm | Effluent ppm | Percent Removed |
|---|---|---|---|---|---|---|---|
| Ionac SR3 | 10 | 1.87 | 12.46 | 9 | 4.1 | 1.6 | 61 |
| Purolite A-501P | 20 | 4.19 | 31.4 | 8 | 3.8 | 2 | 47.4 |
| Purolite S-920 | 20 | 2.96 | 25.7 | 6.9 | 4.2 | 1.5 | 67.3 |
| Purolite S-920 | 20 | 3.62 | 25.7 | 8.45 | 1.9 | 1.3 | 31.6 |
| Dowex 21XLT | 20.7 | 3.81 | 31.4 | 7.3 | 4.1 | 1.6 | 61 |
| ResinTech SIR400 | 20 | 3.35 | 25.12 | 5.7 | 4.3 | 1.6 | 63 |
| Purolite S-920 | 30 | 1.97 | 49.1 | 2.4 | 4.0 | 1.6 | 60 |
| ResinTech SIR400 | 30 | 2.76 | 44.2 | 3.7 | 4.6 | 1.5 | 67.4 |
| Ionac SR-3 | 30 | 2.85 | 44.2 | 3.9 | 3.7 | 1.2 | 67.6 |
| Purolite A-501P | 30 | 4.62 | 56.5 | 4.9 | 1.3 | 1.2 | 7.7 |
| Purolite S-920 | 30 | 1.39 | 44.2 | 1.9 | 3.8 | 1.3 | 65.8 |
| SIR 300 | 30 | 2.89 | 44.2 | 3.9 | 3.6 | 2.0 | 44 |
| SIR 300 | *N.R. | 1.2 | 36.8 | 2.0 | 2.3 | 1.9 | 45 |
| SIR 200 | 30 | 3.75 | 51.5 | 4.4 | 3.5 | 1.4 | 60 |
| SIR 500 | 30 | 3.1 | 51.5 | 3.6 | 3.6 | 1.0 | 72 |
| SIR 500 | 30 | *N.R. | 51.5 | *N.R. | 3.5 | 1.2 | 66 |
| SIR 500 | 30 | 1.45 | 46.6 | 1.9 | 3.6 | 1.0 | 72 |
| Dowex 21XLT | 30 | 2.72 | 58.9 | 2.8 | 3.6 | 0.5 | 86 |
| Dowex M43 | 30 | 2.68 | 46.6 | 3.4 | 3.4 | 0.6 | 82 |
| Dowex 21 XLT** | 30 | 3.62 | 54.0 | 4.0 | 3.4 | 0.6 | 82 |
| Dowex 21K Cl | 30 | 3.33 | 44.2 | 4.5 | 3.5 | 0.6 | 82.9 |
| SIR 400 | 30 | 2.96 | 44.2 | 4.0 | 6.0 | 1.1 | 81.7 |
| Ionac SR-3 | 30 | 2.77 | 38.8 | 4.3 | 5.8 | 1.2 | 79.3 |
| Dowex M43 | 30 | 3.31 | 44.2 | 4.5 | 6.4 | 1.6 | 75.0 |
| Dowex 21K Cl | 30 | 2.91 | 44.2 | 4.0 | 5.8 | 1.6 | 72.4 |
| Dowex 21XLT | 30 | 3.60 | 51.5 | 4.2 | 5.1 | 1.9 | 62.7 |
| Dowex 21K Cl | 30 | 1.16 | 45.2 | 1.5 | 2.7 | 0.2 | 92.6 |
| Dowex 21K Cl | 30 | 1.09 | 46.6 | 1.4 | 2.8 | 0.2 | 92.9 |
| Ionac SR-3 | 30 | 1.04 | 38.8 | 1.6 | 4.2 | 0.9 | 73.8 |
| Purolite S920 | 30 | 2.91 | 44.2 | 4.0 | 2.5 | 0.1 | 96 |
| Dowex 21XLT | 30 | 3.73 | 52.5 | 4.3 | 2.6 | 0.4 | 84.6 |
| Dowex M43 | 30 | 3.17 | 45.7 | 4.2 | 2.8 | 0.4 | 85.7 |
| Purolite S-920 | 30 | 3.09 | 45.2 | 4.1 | 4.1 | 1.1 | 73.2 |
| capacity test | 30 | 3.31 | 45.2 | 4.4 | 4.0 | 1.0 | 75.0 |
|  | 30 | 3.19 | 45.2 | 4.2 | 3.7 | 1.1 | 70.3 |
|  | 30 | 3.24 | 45.2 | 4.3 | 3.8 | 0.9 | 76.3 |
|  | 30 | 3.26 | 45.2 | 4.3 | 2.0 | 0.3 | 85.0 |
|  | 30 | 3.61 | 45.2 | 4.8 | 1.7 | 0.3 | 82.3 |
| Purolite S-920 | 30 | 3.06 | 44.7 | 4.1 | 5.3 | 4.2 | 20.8 |
| SIR-400 | 30 | 3.16 | *N.R. | *N.R. | 2.4 | 0.2 | 91.7 |
| Purolite S-950 | 30 | 2.81 | 41.7 | 4.0 | 2.7 | 0.6 | 77.8 |
| Purolite S-950 | 30 | 4.47 | 42.7 | 6.29 | 2.6 | 0.3 | 88.5 |
| Purolite S-950 | 30 | 3.15 | 45.6 | 4.16 | 2.5 | 0.2 | 92.0 |
| ResinTech SBG-1 | 30 | 3.52 | 48.08 | 4.4 | 1.7 | 0.3 | 82.3 |
| SIR 500 | 30 | 3.59 | 50.53 | 4.26 | 3.4 | 0.2 | 94.1 |
| Purolite S-920 | 30 | 5.57 | 40.3 | 8.3 | 2.5 | 0.3 | 88.0 |

*N.R. denotes that data were not recorded.

The Purolite S-920 capacity test was conducted over several days to measure resin capacity for Platinum adsorption. Most of the column screening tests passed 18-40BV of solids-depleted centrate over the resin bed. However, for the Purolite S-920 capacity test, 515.2 BV of solids-depleted centrate (77.6, 77.6, 77.6, 77.6, 77.6 and 127.2 BV aliquots) were passed over the resin bed. The initial inlet feed solution was depleted and was replaced during the experiment. The results show no reduction in removal efficiency for the duration of this test.

the preparation of N-(phosphonomethyl)glycine by platinum on carbon catalyzed oxidation of N-(phosphonomethyl)iminodiacetic acid in accordance with a process similar to that shown and described in FIG. 1. In addition to the solubilized platinum and N-(phosphonomethyl)glycine product components, such centrates typically also contain low levels of unreacted N-(phosphonomethyl)iminodiacetic acid, formaldehyde, formic acid, N-methyl-N-(phosphonomethyl)glycine (NMG), N-formyl-N-(phosphonomethyl)glycine (NFG), aminomethylphosphonic acid (AMPA), methyl aminomethylphosphonic acid (MAMPA), iminodiacetic acid (IDA) and/or glycine.

The solids depleted stream 17 was passed through an ion exchange column containing Purolite S-920 resin. The liquid flow rate was about 5.3 BV/hr (bed volume per hour). The ion exchange column contained approximately 3 m³ of the resin. The concentration of solubilized platinum in the centrate solution in the inlet to the column and the effluent from the column was analyzed using Inductively Coupled Plasma Mass Spectroscopy (ICP-MS). The concentration of solubilized platinum in the inlet to the column and the effluent from the column and the calculated percentage of solubilized platinum removed from the centrate solution sample by the ion exchange resin are reported in Table 4.

As shown in Table 4, a substantial portion of the platinum was successfully removed from the centrate solution.

TABLE 4

Removal of Solubilized Platinum from Solids-Depleted Centrate

| Date | PLATINUM IN (PPM) | PLATINUM OUT (PPM) | Percent Recovery |
|---|---|---|---|
| Day 8 | 0.03 | 0.02 | 33.3 |
| Day 22 | 1.06 | 0.86 | 18.9 |
| Day 29 | 1.17 | 0.81 | 30.8 |
| Day 42 | 1.19 | 0.79 | 33.6 |
| Day 43 | 1.36 | 0.80 | 41.2 |
| Day 50 | 1.11 | 0.69 | 37.8 |
| Day 58 | 1.11 | 0.63 | 43.2 |
| Day 71 | 1.29 | 0.87 | 32.6 |
| Day 78 | 1.41 | 1.09 | 22.7 |
| Day 85 | 1.44 | 0.93 | 35.4 |
| Day 86 | 1.79 | 1.08 | 39.7 |
| Day 99 | 0.83 | 0.79 | 4.8 |
| Day 99 | 1.34 | 1.25 | 6.7 |
| Day 105 | 3.19 | 1.18 | 63.0 |
| Day 105 | 2.26 | 1.22 | 46.0 |
| Day 112 | 1.46 | 0.69 | 52.7 |
| Day 112 | 1.42 | 0.72 | 49.3 |
| Day 113 | 1.61 | 0.96 | 40.4 |
| Day 121 | 1.76 | 1.14 | 35.2 |
| Day 125 | 1.89 | 1.34 | 29.1 |
| Day 125 | 1.99 | 1.29 | 35.2 |
| Day 125 | 1.96 | 1.26 | 35.7 |
| Day 127 | 1.73 | 1.07 | 38.2 |
| Day 127 | 1.81 | 1.19 | 34.3 |
| Day 127 | 1.65 | 1.18 | 28.5 |
| Day 134 | 1.80 | 0.57 | 68.3 |
| Day 135 | 1.92 | 1.26 | 34.4 |
| Day 135 | 1.72 | 1.31 | 23.8 |
| Day 139 | 1.87 | 1.18 | 36.9 |
| Day 139 | 1.69 | 1.09 | 35.5 |
| Day 140 | 1.91 | 1.12 | 41.4 |
| Day 140 | 1.87 | 1.22 | 34.8 |

Example 5

Removal of Solubilized Platinum from an Aqueous Process Stream Using Activated Carbon Samples of an aqueous process stream containing solubilized platinum were contacted with activated carbon in a laboratory-scale, continuously-operated noble metal recovery stage to evaluate the effectiveness of activated carbon in removing the solubilized platinum. The aqueous process stream utilized in this example was filtered solids-depleted stream 17 (i.e., centrate) obtained from the preparation of N-(phosphonomethyl)glycine by platinum on carbon catalyzed oxidation of N-(phosphonomethyl)iminodiacetic acid in accordance with a process similar to that shown and described in FIG. 1. In addition to the solubilized platinum and N-(phosphonomethyl)glycine product components, such centrates typically also contain low levels of unreacted N-(phosphonomethyl)iminodiacetic acid, formaldehyde, formic acid, N-methyl-N-(phosphonomethyl)glycine (NMG), N-formyl-N-(phosphonomethyl)glycine (NFG), aminomethylphosphonic acid (AMPA), methyl aminomethylphosphonic acid (MAMPA), iminodiacetic acid (IDA) and/or glycine.

Figure 2:
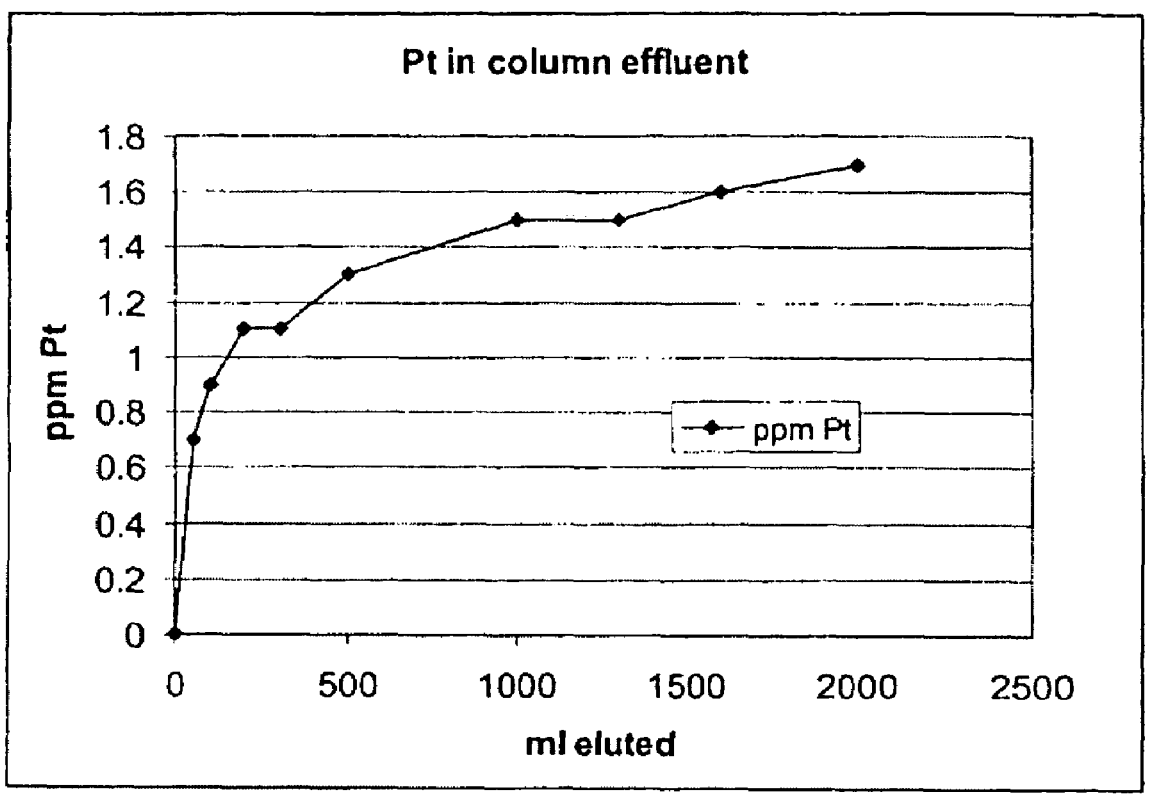
FIG. 2 shows the platinum concentration in the column effluent versus the cumulative flow of aqueous process stream through the activated carbon column in Example 5.

A solids-depleted process solution was pumped using a peristaltic pump from a reservoir at an adjustable rate of 10 ml/min to a gravity fed column packed with activated carbon. The flowrate was adjusted to assure a small level of liquid was present at the top of the gravity fed carbon column. A liquid level was maintained so no air voids would form in the column, thereby reducing the efficiency of the column. The solids-depleted process solution passed through the column and was collected in a receiver vessel. A 1 gram sample of the column effluent was taken at selected time intervals, to evaluate the change in concentration of Platinum from the inlet to the outlet. The change in concentration was assumed to be due to platinum removal. FIG. 2 shows the platinum in the column effluent versus the cumulative flow.

The above description of the preferred embodiments is intended only to acquaint others skilled in the art with the invention, its principles, and its practical application, so that others skilled in the art may adapt and apply the invention in its numerous forms, as may be best suited to the requirements of a particular use. The present invention, therefore, is not limited to the above embodiments, and may be variously modified.

With reference to the use of the word(s) "comprise" or "comprises" or "comprising" in this specification (including the claims), Applicants note that unless the context requires otherwise, those words are used on the basis and clear understanding that they are to be interpreted inclusively, rather than exclusively, and that Applicants intend each of those words to be so interpreted in construing this specification (including the claims).

What is claimed is:

1. A process for recovering noble metal from an aqueous process stream comprising a solubilized noble metal and at least one organic chelating agent and generated in a process for making an N-(phosphonomethyl)glycine product by the heterogeneous noble metal-catalyzed oxidation of an N-(phosphonomethyl)iminodiacetic acid substrate, the recovery process comprising:
 contacting at least a portion of the aqueous process stream generated in the process for making an N-(phosphonomethyl)glycine product by the heterogeneous noble metal-catalyzed oxidation of an N-(phosphonomethyl)iminodiacetic acid substrate with a noble metal adsorption media to remove at least a portion of the solubilized noble metal therefrom and produce a treated aqueous process stream having a reduced concentration of noble metal and a noble metal adsorption media comprising the noble metal; and
 incinerating the noble metal adsorption media comprising the noble metal to form an ash comprising the noble metal.

2. The process as set forth in claim 1 further comprising separating the noble metal from the ash.

3. The process as set forth in claim 1 wherein the noble metal is selected from the group consisting of platinum, palladium, ruthenium, rhodium, iridium, silver, osmium, and gold.

4. The process as set forth in claim 3 wherein the noble metal is platinum or palladium.

5. The process as set forth in claim 4 wherein the noble metal is platinum.

6. The process as set forth in claim 1 wherein at least a portion of the solubilized noble metal in the aqueous process stream is present in the form of an ion or colloid.

7. The process as set forth in claim 1 wherein the concentration of solubilized noble metal in the aqueous process stream is at least about 0.1 ppm prior to contacting the stream with the noble metal adsorption media.

8. The process as set forth in claim 7 wherein the concentration of solubilized noble metal in the aqueous process stream is from about 0.1 ppm to about 100 ppm prior to contacting the stream with the noble metal adsorption media.

9. The process as set forth in claim 8 wherein the concentration of solubilized noble metal in the aqueous process stream is from about 1 ppm to about 20 ppm prior to contacting the stream with the noble metal adsorption media.

10. The process as set forth in claim 9 wherein the concentration of solubilized noble metal in the aqueous process stream is from about 3 ppm to about 6 ppm prior to contacting the stream with the noble metal adsorption media.

11. The process as set forth in claim 1 wherein the portion of solubilized noble metal removed by the noble metal adsorption media is at least about 20 percent by weight of the solubilized noble metal in the aqueous process stream.

12. The process as set forth in claim 11 wherein from about 60 percent to about 85 percent by weight of the solubilized noble metal is removed from the aqueous process stream.

13. The process as set forth in claim 1 wherein the reduced concentration of solubilized noble metal in the treated aqueous process stream is less than about 80 ppm.

14. The process as set forth in claim 13 wherein the reduced concentration of solubilized noble metal in the treated aqueous process stream is less than about 10 ppm.

15. The process as set forth in claim 14 wherein the reduced concentration of solubilized noble metal in the treated aqueous process stream is from about 0.1 ppm to about 5 ppm.

16. The process as set forth in claim 15 wherein the reduced concentration of solubilized noble metal in the treated aqueous process stream is from about 1 ppm to about 3 ppm.

17. The process as set forth in claim 1 wherein the noble metal adsorption media comprises a material selected from the group consisting of activated carbon, an ion exchange resin and mixtures thereof.

18. The process as set forth in claim 17 wherein the noble metal adsorption media comprises an ion exchange resin.

19. The process as set forth in claim 18 wherein the ion exchange resin is selected from the group consisting of strong base anion exchange resins, weak base anion exchange resins, strong acid cation exchange resins, weak acid cation exchange resins, chelating exchange resins and mixtures thereof.

20. The process as set forth in claim 18 wherein the ion exchange resin comprises a functional group selected from the group consisting of thiouronium, isothiouronium, thiol, α-hydroxy thiol, iminodiacetate, quaternary amine, aminophosphonic and mixtures thereof.

21. The process as set forth in claim 1 wherein the at least one organic chelating agent present in the aqueous process stream is selected from the group consisting of N-(phosphonomethyl)glycine product, unreacted N-(phosphonomethyl)iminodiacetic acid substrate, N-methyl-N-(phosphonomethyl)glycine (NMG), N-formyl-N-(phosphonomethyl)glycine (NFG), aminomethylphosphonic acid (AMPA), methyl aminomethylphosphonic acid (MAMPA), iminodiacetic acid (IDA), glycine and mixtures thereof.

22. The process as set forth in claim 21 wherein at least a portion of the solubilized noble metal in the aqueous process stream is present in the form of a chelated complex formed with ligands of one or more chelating agents selected from the group consisting of N-(phosphonomethyl)glycine product, unreacted N-(phosphonomethyl)iminodiacetic acid substrate, N-methyl-N-(phosphonomethyl)glycine (NMG), N-formyl-N-(phosphonomethyl)glycine (NFG), aminomethylphosphonic acid (AMPA), methyl aminomethylphosphonic acid (MAMPA), iminodiacetic acid (IDA), and glycine.

23. The process as set forth in claim 21 wherein the aqueous process stream comprising solubilized noble metal further comprises N-(phosphonomethyl)glycine product.

24. The process as set forth in claim 23 wherein the aqueous process stream contacted with the noble metal adsorption media is maintained at a temperature sufficient that the N-(phosphonomethyl)glycine product remains in solution.

25. The process as set forth in claim 24 wherein the aqueous process stream contacted with the noble metal adsorption media is maintained at a temperature of at least about 25° C.

26. The process as set forth in claim 25 wherein the aqueous process stream contacted with the noble metal adsorption media is maintained at a temperature of from about 60° C. to about 95° C.

27. The process as set forth in claim 1 wherein the aqueous process stream further comprises solids and wherein the aqueous process stream is passed through a noble metal adsorption media prefilter prior to being contacted with the noble metal adsorption media to remove the solids.

28. The process as set forth in claim 1 wherein the aqueous process stream comprises an aqueous solids-depleted stream comprising N-(phosphonomethyl)glycine product and solubilized noble metal, wherein preparation of the aqueous solids-depleted stream comprises:
   oxidizing the N-(phosphonomethyl)iminodiacetic acid substrate in an oxidation reactor system in the presence of a heterogeneous oxidation catalyst comprising a noble metal to produce a reaction product mixture comprising the noble metal catalyst and a reaction product solution comprising N-(phosphonomethyl)glycine product and solubilized noble metal;
   precipitating N-(phosphonomethyl)glycine product crystals from the reaction product solution to produce a product slurry comprising precipitated N-(phosphonomethyl)glycine product crystals and a mother liquor containing N-(phosphonomethyl)glycine product and solubilized noble metal; and
   separating N-(phosphonomethyl)glycine product crystals from the product slurry to produce an N-(phosphonomethyl)glycine product wet-cake and the aqueous solids-depleted stream comprising the mother liquor.

29. The process as set forth in claim 1 wherein the aqueous process stream comprises an aqueous oxidized overhead stream comprising solubilized noble metal, wherein preparation of the aqueous oxidized overhead stream comprises:
   oxidizing the N-(phosphonomethyl)iminodiacetic acid substrate in an oxidation reactor system in the presence of a heterogeneous oxidation catalyst comprising a noble metal to produce a reaction product mixture comprising the noble metal catalyst and a reaction product solution comprising N-(phosphonomethyl)glycine product;
   concentrating the reaction product solution to precipitate N-(phosphonomethyl)glycine product crystals from the reaction product solution and produce an aqueous overhead stream comprising a compound selected from the group consisting of formaldehyde, formic acid and mixtures thereof and a product slurry comprising precipitated N-(phosphonomethyl)glycine product crystals and a mother liquor; and
   contacting the aqueous overhead stream with an oxidation catalyst comprising a noble metal to convert at least a portion of the formaldehyde and/or formic acid to carbon dioxide and water and produce the oxidized overhead stream comprising solubilized noble metal.

* * * * *